United States Patent [19]
Metcalf

[11] Patent Number: 5,571,508
[45] Date of Patent: Nov. 5, 1996

[54] METHOD FOR THE TREATMENT OF THROMBOCYTOPENIA AND PHARMACEUTICAL COMPOSITIONS USEFUL THEREFOR

[75] Inventor: Donald Metcalf, Balwyn, Australia

[73] Assignee: Amrad Corporation Limited, Victoria, Australia

[21] Appl. No.: 853,774

[22] PCT Filed: Dec. 8, 1990

[86] PCT No.: PCT/AU90/00592

§ 371 Date: Jul. 27, 1992

§ 102(e) Date: Jul. 27, 1992

[87] PCT Pub. No.: WO91/08752

PCT Pub. Date: Jun. 27, 1991

[30] Foreign Application Priority Data

Dec. 18, 1989 [AU] Australia ............................ PJ7912/89
Nov. 23, 1990 [AU] Australia ............................ PK3501/90

[51] Int. Cl.$^6$ ..................................... A61K 45/05
[52] U.S. Cl. ..................... 424/85.2; 514/8; 514/21
[58] Field of Search ............. 424/85.2; 514/21, 514/8

[56] References Cited

U.S. PATENT DOCUMENTS 5,126,325  6/1992  Kishimoto et al. ............... 424/85.1

FOREIGN PATENT DOCUMENTS 8800093  10/1988  WIPO.

OTHER PUBLICATIONS

Metcalf et al. (1989) "A Myelosclerotic Syndrome in Mice Engrafted with Cells Producing High Levels of Leukemia Inhibitory Factor (LIF)" *Leukemia* 3:847–852.

Baumann, et al. (1989) "Hepatocyte–Stimulating Factor III Shares Structural and Functional Identity with Leukemia–Inhibitory Factor", *J. Immunol.* 143, 1163–1167.

Yamamori et al. (1989) "The Cholinergic Neuronal Differentiation Factor From Heart Cells Is Identical to Leukemia Inhibitory Factor" *Science* 246, 1412–1416.

McDonald T. P., Magakaryocyte biology and Precursors: in vitro cloning and cellular properties, Eds. Evatt B. L. et al., Elsevier, pp. 39–57, 1981.

Wintrobe et al., Clinical Hemetology, Eighth Edition, Chapter 47, 1981.

Whicher et al., Clin Chem., vol. 36(7), pp. 1269–1281, 1990.

Hamblin, Lymphohines, IRL Press, 1988, pp. 22–23, 32–33, 45–48, 51–52.

Burstein et al., J. Cellular Physiology, vol. 153, pp. 305–312, 1992.

Metcalf et al., Blood, vol. 77(10), pp. 2150–2153, 1991.

Stiles et al., Basic & Clinical Immunology, Seventh Edn., Chapter 7, 1991.

McDonald Advances in Experimental Med. & Biol. vol. 241, 1988, pp. 243–253.

Ishibashi et al. Blood, vol. 74, No. 4 Sep. 1989, pp. 1241–1244.

*Primary Examiner*—Chhaya D. Sayala
*Attorney, Agent, or Firm*—Scully, Scott, Murphy & Presser

[57] ABSTRACT

The present invention relates generally to a method for, and pharmaceutical compositions useful in, the treatment of thrombocytopenia in a mammal by the administration of an effective amount of leukaemia inhibitory factor (LIF) and/or its derivatives and optionally in combination with one or more other cytokines.

10 Claims, 11 Drawing Sheets

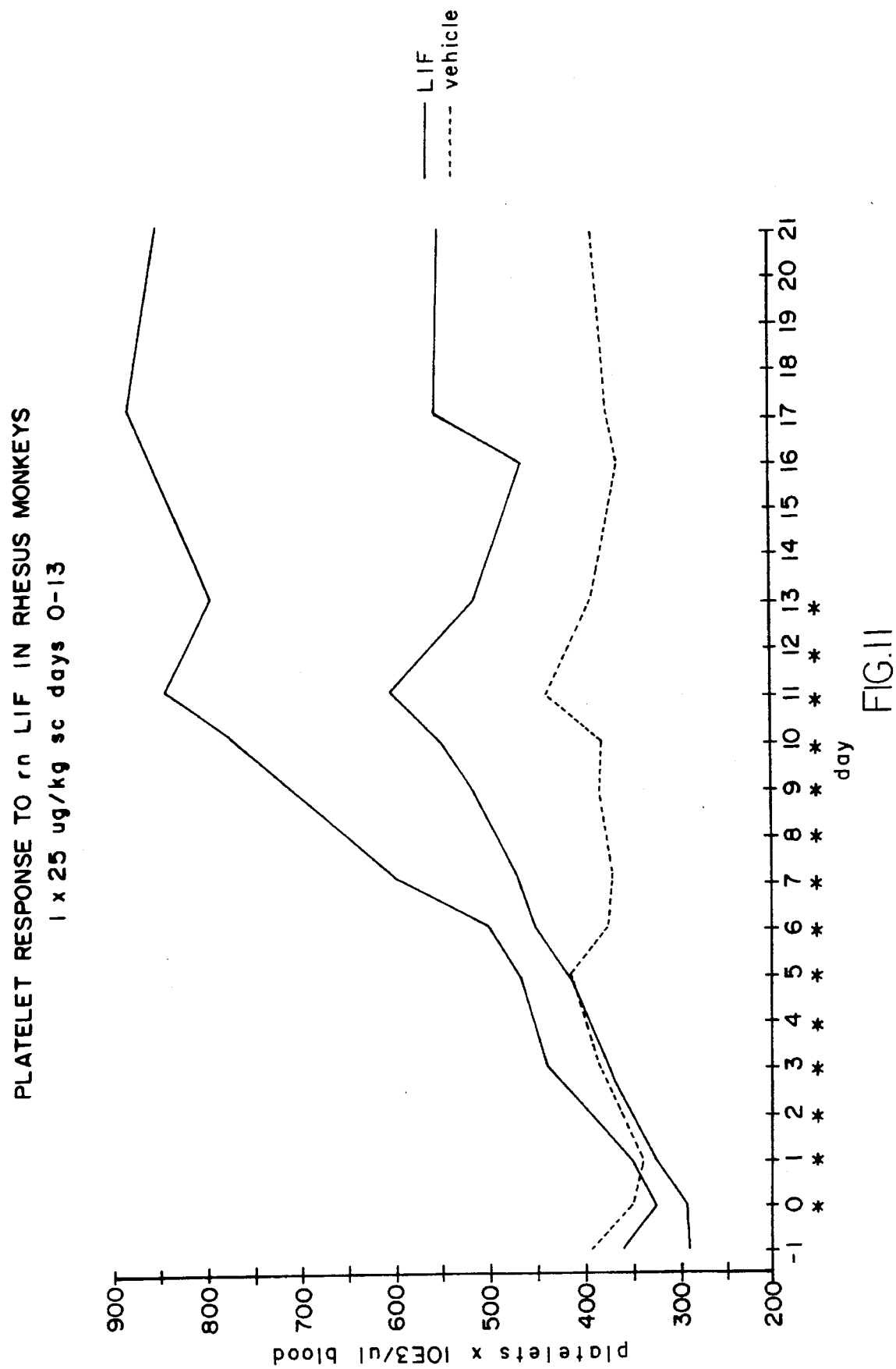

METHOD FOR THE TREATMENT OF THROMBOCYTOPENIA AND PHARMACEUTICAL COMPOSITIONS USEFUL THEREFOR

The present invention relates generally to a method for, and pharmaceutical compositions useful in, the treatment of thrombocytopenia in a mammal by the administration of an effective amount of leukaemia inhibitory factor (LIF) and/or its derivatives and optionally in combination with one or more other cytokines.

Leukaemia inhibitory factor (LIF) was purified (1, 2) and cloned (3) on the basis of its capacity to induce differentiation in and suppress clonogenecity of the M1 mouse myeloid leukaemic cell line (see International Patent Application No. PCT/AU88/00093). LIF has comparable effects on human HL60 and U937 cells, particularly when acting in collaboration with colony stimulating factors (4). In conventional semisolid cultures, LIF has no colony stimulating activity for normal murine haemopoietic cells (5) although it stimulates the proliferation of the continuous haemopoietic cell line DA1.1a (6) and erythroid cell lines from myc-transformed mouse fetal liver cells.

Receptors for LIF are present on monocytemacrophages (7) and some non-haemopoietic cells including osteoblasts, placental and liver cells (8). LIF has been shown to possess a remarkable variety of actions: it releases calcium from bone tissue (9), is the factor preventing spontaneous differentiation in normal embryonic stem cells (10, 11), is a molecule stimulating DA1.1a (6) cell proliferation, stimulates liver cells to produce acute phase proteins (12, 13), and is a lipoprotein lipase inhibitor (14).

In initial studies, the consequences of high LIF levels were determined in mice engrafted with FDC-P1 cells producing LIF (International Patent Application No. PCT/U90/00092; 15, 16). Such mice developed a fatal syndrome of body weight loss, osteosclerosis with compensatory splenic and liver extramedullary haemopoiesis, a neutrophil leukocytosis, pancreatitis, calcification in skeletal muscle, heart and liver, liver necrosis and fibrosis, thymus atrophy, adrenal cortex changes and failure of spermatogenesis and corpora lutea formation.

The engrafted model is potentially complex due to the presence of the engrafted FDC-P1 cells. The present invention arose from experiments attempting to overcome this complexity by injecting purified recombinant murine LIF into mice to determine what changes could be induced by injected LIF. Changes inter alia in blood components, marrow, spleen and peritoneal cell components, megakaryocyte and progenitor cell components in the marrow and spleen were analysed and it was surprisingly discovered that LIF caused the enhancement, stimulation and/or increase in the level of formation of megakaryocytes and/or their progenitor cells and led to an increase in platelets. The present invention, therefore, will be beneficial in the treatment of thrombocytopenia occurring in some acute infections, anaphylactic shock, certain haemorrhagic diseases, anaemias, as a result of chemo- or radiotherapy, platelet- function deficient disease, chronic hepatic disorders and renal disorders.

Accordingly, one aspect of the present invention relates to a method for treating thrombocytopenia in a mammal which method comprises administering to said mammal an effective amount of leukaemia inhibitory factor (LIF) for a time and under conditions sufficient to enhance, stimulate and/or increase the level of formation of megakaryocytes and/or their progenitor cells and/or increase the level of platelets.

In another embodiment, LIF is administered simultaneously or sequentially with one or more other cytokines.

Another aspect of the present invention is directed to a pharmaceutical composition for treating thrombocytopenia in a mammal said composition comprising LIF in combination with one or more other cytokines and one or more pharmaceutically acceptable carriers and/or diluents.

Yet another aspect of the present invention relates to the use of LIF alone or in combination with one or more other cytokines and/or their derivatives for the manufacture of a medicament for treating thrombocytopenia by enhancing, stimulating and/or increasing the level of formation of megakaryocytes and/or its progenitors and/or platelets in a mammal.

In a preferred embodiment, the mammal is a human or a livestock animal and human, murine and/or a livestock animal LIF is used. Furthermore, preferred other cytokines include interleukin 3 (IL-3), thrombopoietin and/or interleukin 6(IL-6). The most preferred other cytokine is IL-3. In any event, the preferred other cytokine is of human, murine and/or livestock animal origin.

The present invention is described in terms of the effect of LIF in mice and monkeys. This is done with the understanding, however, that the present invention extends to the effect of LIF in all mammals and in particular humans and livestock animals. Accordingly, by reference herein to the effect of LIF in mice or monkeys is meant to be applicable to the effect of LIF in mammals and in particular humans and livestock animals.

In one embodiment, human, murine or livestock animal LIF is used although the present invention extends to any mammalian LIF having the desired activity herein described.

The term "thrombocytopenia" is used herein to denote conditions in a mammal affecting levels of megakaryocytes and/or their progenitors and/or platelets. Accordingly, the treatment of thrombocytopenia is taken to be enhancing, stimulating and/or increasing the level of formation of megakaryocytes and/or their progenitor cells and/or increasing the level of platelets in a mammal by the administration of an effective amount of LIF for a time and under conditions sufficient to effect an increase in the number of megakaryocytes and/or their progenitors and/or platelets. Thrombocytopenia may occur following a disease condition or result from trauma or therapy and the present invention is not limited to any one or more causes of thrombocytopenia. Typically, thrombocytopenia will occur in some acute infections anaphylactic shock, certain haemorrhagic diseases, anaemias, as a result of chemo- or radiotherapy, platelet-function deficient disease, chronic hepatic disorders and renal disorders.

The present invention also extends to preventative therapy whereby LIF and optionally one or more cytokinnes are administered to prevent or reduce the likelihood of thrombocytopenia developing.

The very short serum half-life of intravenously-injected LIF indicated that the intraperitoneal route was more practicable in mice for ensuring sustained periods of elevated serum LIF levels. However, other routes of administration may be possible without departing from the scope of the present invention (eg. intravenous, intramuscular and subcutaneous) and all such routes are encompassed herein. Irradiated mice engrafted with LIF-producing cells developed serum levels of up to $10^3$ units/ml and some developed organ changes within 14 days (15, 16). The initial schedule chosen to attempt to document in vivo effects of injected LIF was 2 µg three times daily for 14 days which would achieve LIF levels above $10^3$ units/ml for several hours after each injection. The extreme side effects encountered suggest that these were toxic. The unexpected and unanticipated changes observed in the work leading to the present invention such as those in platelet levels were not recognised initially and not all mice were analysed for these changes.

In accordance with the present invention, it has been discovered that a clear elevation of progenitor cells is induced in the spleen by the injection of LIF, alone or in combination with one or more other cytokines, and this includes rises in megakaryocyte progenitors. While the progenitor cell changes do not result in observable increases in mature neutrophils, monocytes or eosinophils, they are associated with a rise in megakaryocyte numbers, followed by a rise in blood platelet levels. The magnitude of the megakaryocyte and platelet rises induced by LIF is alone or in combination with one or more other cytokines equal to or greater than those induced by IL-3 (18), thrombopoietin (19) or IL-6 alone (20, 21) indicating the potential clinical use of LIF to treat thrombocytopenia by increasing the level of megakaryocytes and/or their progenitor cells and/or platelets. In this context, it is of interest that reduced doses of LIF are still able to induce changes in megakaryocyte and platelet levels without toxic effects as assessed by behavioural changes or body or thymus weight loss. A particularly effective combination is LIF and IL-3.

While LIF appears to have no colony stimulating activity in conventional semisolid cultures of unfractionated mouse marrow cells or purified progenitor cells (Hilton DJ, Nicola NA and Metcalf D, unpublished data), the present invention demonstrates that megakaryocytes do express LIF receptors. Although it is not the intention to limit the present invention to any one theory behind the mode of action, the stimulating effects of LIF on megakaryocyte and platelet formation could represent direct effects possibly in association with some other factors. LIF induces rises in megakaryocyte progenitor cells and megakaryocytes before rises in platelet levels, suggesting that the observed rises in platelets are based on the increased formation of megakaryocytes and not merely the induced release of platelets from existing megakaryocytes. Furthermore, the effects of injected LIF on progenitor cell levels, megakaryocyte formation and platelet levels described herein are in contrast to the apparent inactivity of LIF on normal haemopoietic cells in vivo. Another possibility may be that LIF may interact with or elicit production of some other megakaryocyte stimulatory factors.

Accordingly, the present invention contemplates a method of treating thrombocytopenia in a mammal which method comprises administering to said mammal an effective amount of LIF alone or in combination with one or more other cytokines for a time and under conditions sufficient to increase the numbers of megakaryocytes and/or their progenitors and/or platelets.

Preferably the mammal is a human or a livestock animal although the present invention is not so limited. Furthermore, the route of administration is preferably by interperitoneal, intravenous, intramuscular or subcutaneous administration (eg injection) but other routes may be equally applicable with only minor modification to the method as contemplated herein. The effective amount of LIF will depend on the mammal and the condition to be treated. For example, in mice, the frequency of megakaryocytes was increased in the spleen 2–5 fold after i.p. injection one to three times daily with 2 µg LIF for 3–14 days. However, the amount required to be administered to the mammal will need to be non-toxic. Hence, in mice, for example, a dose of 200 ng or lower given one to three times daily for 14 days while causing a slightly smaller increase in megakaryocytes and platelets compared to the near toxic dosages was never-the-less effective and, importantly, non-toxic. In general, the effective amount of LIF and, where used, the cytokine will be 0.01 to 10,000 µg/kg and preferably, 1 to 1000 µg/kg body weight.

Use herein of the term "livestock animal" is intended to include such animals as sheep, pigs, goats, horses, donkeys and cows and further extends to cats and dogs.

The method of the present invention further contemplates the simultaneous or sequential administration of LIF with one or more other cytokines. Such cytokines include, but are not limited to, IL-3 thrombopoietin and/or IL-6. In a most preferred embodiment, LIF is given with IL-3. Such a mode of administration encompasses the administration of a single composition comprising both LIF and the cytokine (simultaneous administration) or the administration of two separate compositions, one containing LIF and the other containing one or more other cytokines (sequential administration). The present invention extends to the use of more than one cytokine in separate compositions or in a single composition. Furthermore, the present invention contemplates the use of LIF and the cytokine in any order. In another embodiment one cytokine (including LIF) may be given by direct injection while the other cytokine is administered by, for example, a drip. In sequential administration the present invention is not limited to any time period between the administration of the two compositions. Preferably, however, the time difference would be less than 72 hours.

In all of the above cases, the present invention also extends to the use of derivatives, homologues and/or analogues of LIF and the other cytokines. By "derivative" and "analogue" are meant recombinant, chemical or other synthetic forms of LIF or other cytokine and/or any alterations such as addition, substitution and/or deletion to the amino acid sequence component of the molecule or to the carbohydrate or other associated molecule moiety (if present) of LIF or other cytokine, provided the derivative possesses megakaryocyte, megakaryocyte progenitor and/or platelet stimulating activity. Preferably, the LIF is of human, murine or livestock origin but the present invention is not necessarily limited thereto. Use herein, therefore, of the terms "LIF" and "cytokine" is intended to encompass any one or more of their derivatives, homologues or analogues including naturally occurring (natural) or recombinant or synthetic forms.

In accordance with the present invention, the LIF and one or more other cytokines (eg IL-3) may be from the same or different mammalian species.

The present invention further extends to pharmaceutical compositions comprising LIF in combination with one or more other cytokines and/or their derivatives and one or more pharmaceutically acceptable carriers and/or diluents. Such pharmaceutical compositions will be useful in enhancing, stimulating and/or increasing the level of formation of megakaryocytes and/or its progenitor cells and/or platelet cells.

The method and pharmaceutical compositions described in accordance with the present invention will be useful in the treatment inter alia of thrombocytopenia which occurs in some acute infections, anaphylactic shock, certain haemorrhagic diseases, leukaemia anaemias, as a result of chemo- or radiotherapy, platelet-function deficient disease, chronic hepatic disorders and renal disorders. Furthermore, the present invention extends to the use of LIF and/or its derivatives alone or in combination with one or more other cytokines and/or their derivatives for the manufacture of a medicament for enhancing, stimulating and/or increasing the level of formation of megakaryocytes and/or its progenitors and/or platelets in a mammal, and in particular humans and livestock animals, such as in the treatment of thrombocytopenia.

The presence of LIF after administration by i.p. injection had other affects as outlined below.

The haemopoietic changes observed in LIF-injected mice (see Example 2) had a pattern which indicated that LIF has either direct or indirect actions affecting certain haemopoietic populations. Injections of 2 µg LIF in mice, for example, failed to reproduce the characteristic neutrophil leukocytosis seen in the engrafted model (16) but did reproduce other changes seen in such mice including reduced marrow cellularity with selective loss of marrow lymphocytes, depression of spleen lymphocyte populations with increased splenic erythropoiesis and marked thymus atrophy due to loss of cortical lymphocytes.

Furthermore, early effects of high doses of LIF were a hyperactive state and body weight loss, the latter based on a reduction in subcutaneous and abdominal fatty tissue. The hyperactive state may be related to the ability of LIF to switch autonomic nerve signalling from adrenergic to cholinergic mode or be related to the hypercalcemia (22). The selective loss of body fat may be based on the lipoprotein lipase inhibitory activity of LIF (14) which may prevent the transport of lipid into fat cells. The increased erythrocyte sedimentation rate noted in LIF-injected mice was apparent within 6 hours of a single injection and may be due to the ability of LIF to induce the production by liver cells of acute phase proteins (12, 13) likely to influence erythrocyte sedimentation.

No abnormalities were noted in other organs of LIF-injected mice other than minimal calcification in the myocardium and this was seen only in mice injected with the highest doses of LIF.

One of the most striking changes in LIF-engrafted mice was the excess osteoblast activity and new bone formation occurring particularly in the sternum and end of the long bones (15, 16). Marked changes of this nature were not observed in LIF-injected mice but LIF injections possibly induced some thickening of the cortex of sternal bone segments. After the intravenous injection of $^{125}$I-labelled LIF, labelling of marrow osteoblasts was observed so injected LIF has access to these cells and LIF may therefore have direct actions on osteoblasts and new bone formation. In this context, initial experiments injecting LIF for 3 days to preirradiated, but not normal mice, has produced a definite increase in reticulum in the bone marrow, a change seen in dramatic form in the marrow of mice engrafted with LIF-producing cells. The ability of even low doses of LIF to elevate serum calcium levels may be of significance for an action of LIF in promoting new bone formation.

The present invention is further described by the following non-limiting Figures and Examples.

In the Figures:

FIG. 11 is a graphical representation showing the platelet response to rhLIF in Rhesus monkeys.

EXAMPLE 1

Materials and Methods

Mice

Figure 1:
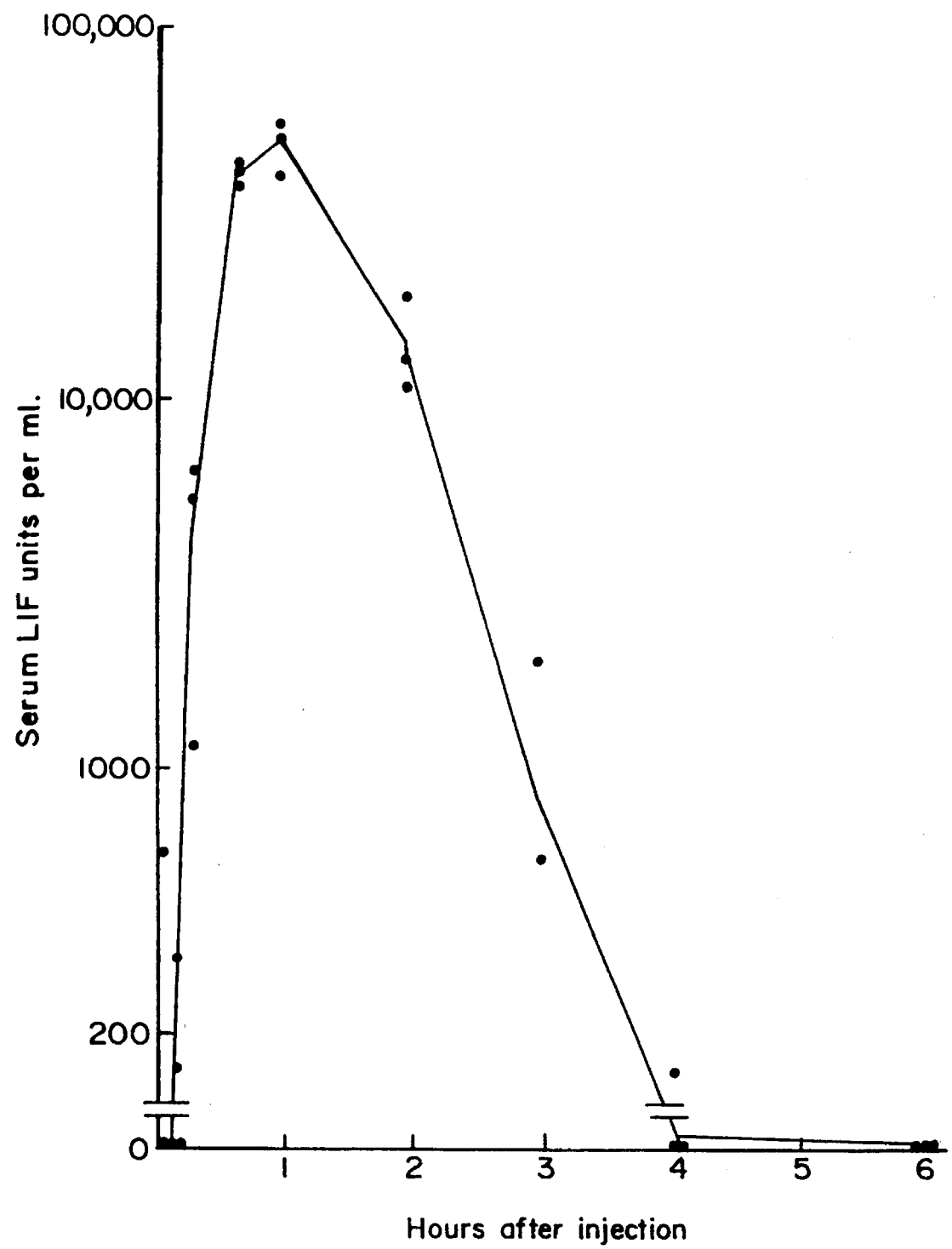
FIG. 1 is a graphical representation showing serum LIF levels in DBA/2 mice following the intraperitoneal injection of 2 µg LIF. Each point represents serum levels from a different mouse.

Mice used were specific pathogen-free 2 to 3 month old females of the strain DBA/2 (the strain previously used as recipients of LIF-producing FDC-P1 cells as described in International Patent Application No. PCT/AU90/00092) and the endotoxin hyporesponsive strain, C3H/HeJ, the latter to minimise the possibility that any observed changes might be ascribable to endotoxin.

Recombinant LIF

Recombinant murine LIF was produced using the GEX bacterial expression system and purified to homogeneity as previously described (PCT/AU88/00093). The specific activity of the LIF was approximately $10^8$ units/mg protein as assayed on M1 leukaemic cells (50 units/ml is the concentration of LIF inducing the differentiation of 50% of M1 colonies in agar cultures of 300 M1 cells—see PCT/AU88/00093).

The recombinant LIF was dissolved in 5% (v/v) fetal calf serum (FCS/saline) so that each dose injected was in a volume of 0.2 ml. Control mice were injected with 0.2 ml of the same 5%(v/v) FCS/saline diluent batch. Two separate preparations of LIF were used and two different batches of FCS/saline used as diluent. All preparations were assayed by the Limulus amoebocyte lysate assay and the injection volumes of 0.2 ml of LIF in FCS/saline or 0.2 ml FCS/saline were found to contain 0.1–0.2 ng endotoxin, indicating that the endotoxin content of the material probably originated from the FCS used.

Injections

Mice were injected one to three times daily for up to 14 days with 0.2 ml of LIF or FCS/saline, weighed at intervals then analysed in detail on the morning after completion of the last day of injections.

Cultures

All cultures were performed using 35 mm Petri dishes containing 50,000 bone marrow cells from 2 months old C3H/HeJ mice in 1 ml of agar-medium with a final concentration of 20% (v/v) fetal calf serum in 0.3% (w/v) agar.

Cultures were incubated at 37° C. in a fully humidified atmosphere of 10% (v/v) $CO_2$ in air. After 1 week of incubation, colony counting was performed at ×35 magnifications then all cultures fixed using 1 ml of 2.5% (w/v) glutaraldehyde in 0.9% (w/v) saline. After floating the intact cultures onto glass slides, the cultures were air-dried and stained for acetylcholinesterase, then with Luxol-Fast-Blue and haematoxylin. Using coded slides, megakaryocyte colonies (defined as clones containing two or more acetylcholinesterase-positive cells) were enumerated and total cell counts performed of acetylcholinsterase-positive cells in each colony.

All stimuli tested were purified murine recombinant factors produced in this laboratory using bacterial or yeast expression systems: specific activities for LIF, IL-3, GM-CSF, G-CSF and M-CSF were all $10^8$ Units/mg.

Autoradiography

Purified recombinant murine LIF was labelled with $^{125}I$ using methods described previously(3). Adult mice were injected intravenously with $10^8$ counts/min $^{125}I$-LIF and killed 1 hour later. Tissues were fixed in 10 formal saline, 5µ sections prepared and dipped in Kodak N2 emulsion. After exposure for 3 months, the slides were developed and stained with haematoxylin and eosin. For in vitro studies, spleen and marrow suspensions were incubated for 1 hour at 37° C. with $^{125}$-LIF (100,000 counts/min) with or without a 20-fold excess of unlabelled LIF. The cells were washed, cytocentrifuge preparations fixed using 2.5% (w/v) glutaraldehyde. After dipping and exposure, the preparations were stained with May-Grunwald Giemsa.

Observations

Mice were anaesthetised and orbital plexus blood used for white cell, haematocrit and platelet estimations. Mice were exsanguinated from the axillary vessels and the serum diluted 1:4 for further analysis. Peritoneal cavity cells were collected using 2 ml of 5% (v/v) FCS/saline, organs were weighed and total femur cell counts performed. Cytocentrifuge preparations were made from peritoneal, spleen and marrow cells and stained with May-Grunwald/Giemsa. All preparations were scored using coded slides. Organs were fixed in 10% (v/v) formal saline, sectioned then stained with haematoxylin and eosin for reticulum. Spleen and marrow cell suspensions were cultured to determine the frequency of progenitor cells using 1 ml agar-medium cultures of 25,000 cells stimulated by a mixture of 400 units GM-CSF and 400 units IL-3 (17). At day 7, colony counts were performed and the cultures mixed with 1 ml of 2.5% (w/v) glutaraldehyde then stained sequentially for acetylcholinesterase then Luxol Fast blue and haematoxylin, differential colony counts were performed at ×200 magnification on coded preparations.

Erythrocyte sedimentation was measured in heparinized capillary haematocrit tubes using a 50 mm column of blood. Accelerated sedimentation of red cells was noted within 10 min with blood from LIF-injected mice but measurements were made routinely at 2 hours. For simplicity, the figures were transformed arithmetically to mm sedimentation per 100 mm column.

Serum calcium and albumin estimations were performed using 1–4 diluted serum.

Megakaryocyte cell counts were performed at ×400 magnifications from sections of spleen and sternal marrow segments. The area surveyed was determined from camera lucida drawings and the figures expressed as megakaryocytes X area$^{-1}$ X organ weight for spleen or megakaryocytes X area$^{-1}$ X 100 for individual sternal marrow segments.

Statistical Analysis

All data were analysed using the student T test to establish the statistical significance of observed differences.

EXAMPLE 2

Effect of LIF

The mean serum LIF concentrations in mice engrafted with LIF-producing FDC-P1 cells were 1000 units/ml (15, 16). To determine if comparable concentrations could be achieved by the injection of LIF, studies were performed on the serum half-life of LIF injected intravenously or intraperitoneally. Intravenous injection of 2 µg of LIF resulted in a very short serum half-life with a second phase of 8–9 minutes. However the intraperitoneal injection of 2 µg LIF resulted in a more sustained elevation of serum LIF levels which exceeded 1000 units/ml for approximately 3 hours (FIG. 1). On this basis, initial injections were performed three times daily at 8.00 am, 2.00 pm and 5.00 pm using 2 µg LIF injected intraperitoneally. In subsequent experiments lower doses of LIF were used and the number of injections per day varied from 1–3.

General Observations

The dose of 2 µg LIF three times daily appeared to be close to the toxic limit since deaths occurred at day 3 of the smallest of 16 DBA/2 mice, of 4 of 8 possibly abnormal C3H/HeJ mice between days 5 and 9, and of the smallest of another group of 8 C3H/HeJ mice on day 5.

Figure 2:
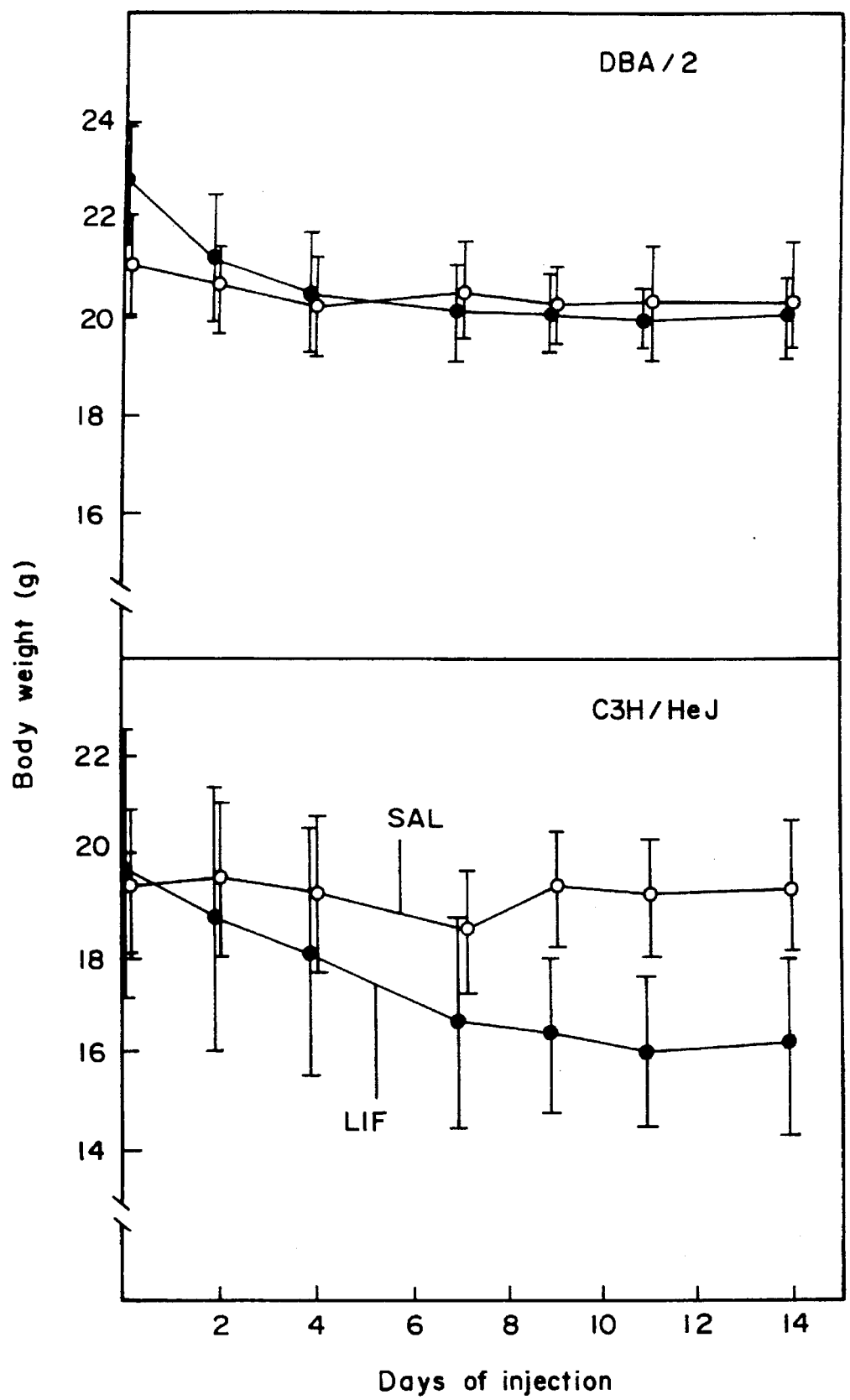
FIG. 2 is a graphical representation showing the loss of body weight in DBA/2 and C3H/HeJ mice injected three times daily with 2 µg LIF. Note that body weight loss is restricted to the first week.

At this dose level, a uniform effect of injected LIF in mice of both strains in five separate experiments was an initial weight loss evident by day 2 and progressive during the first week of injections but with no further weight loss during the second week (FIG. 2). Accompanying the weight loss was a curious state of hypermobility and irritability of the mice with the hair on the back and particularly on the back of the neck being erect. No fighting was exhibited. The LIF-injected mice also exhibited difficulty in recovering from the anaesthetic used—methoxyfluorane.

No deaths or weight loss occurred in mice injected with 200 ng or lower doses of LIF, given 1–3 times daily for 14 days and no irritability of behaviour was observed at these dose levels.

Blood Changes

The changes observed at day 15 in mice injected with 2 µg LIF three times daily are summarised in Table 1. No significant changes occurred in total white cells but a small fall in haematocrit was observed in LIF-injected mice. A notable finding was an increase in platelet levels of most 100% in LIF-injected mice. Platelet levels were not elevated at 6 and 24 hours after a single injection of 2 µg LIF or after 3 days of injections of 2 µg LIF given three times daily (Tables 1,2).

Another feature of blood samples from mice injected with 2 µg LIF was an acceleration of erythrocyte sedimentation. In other experiments, accelerated erythrocyte sedimentation was noted at 6 and 24 hours following a single injection of 2 μg LIF and at 14 days with as low a dose of LIF as 200 ng given once daily (Table 2).

Figure 3:
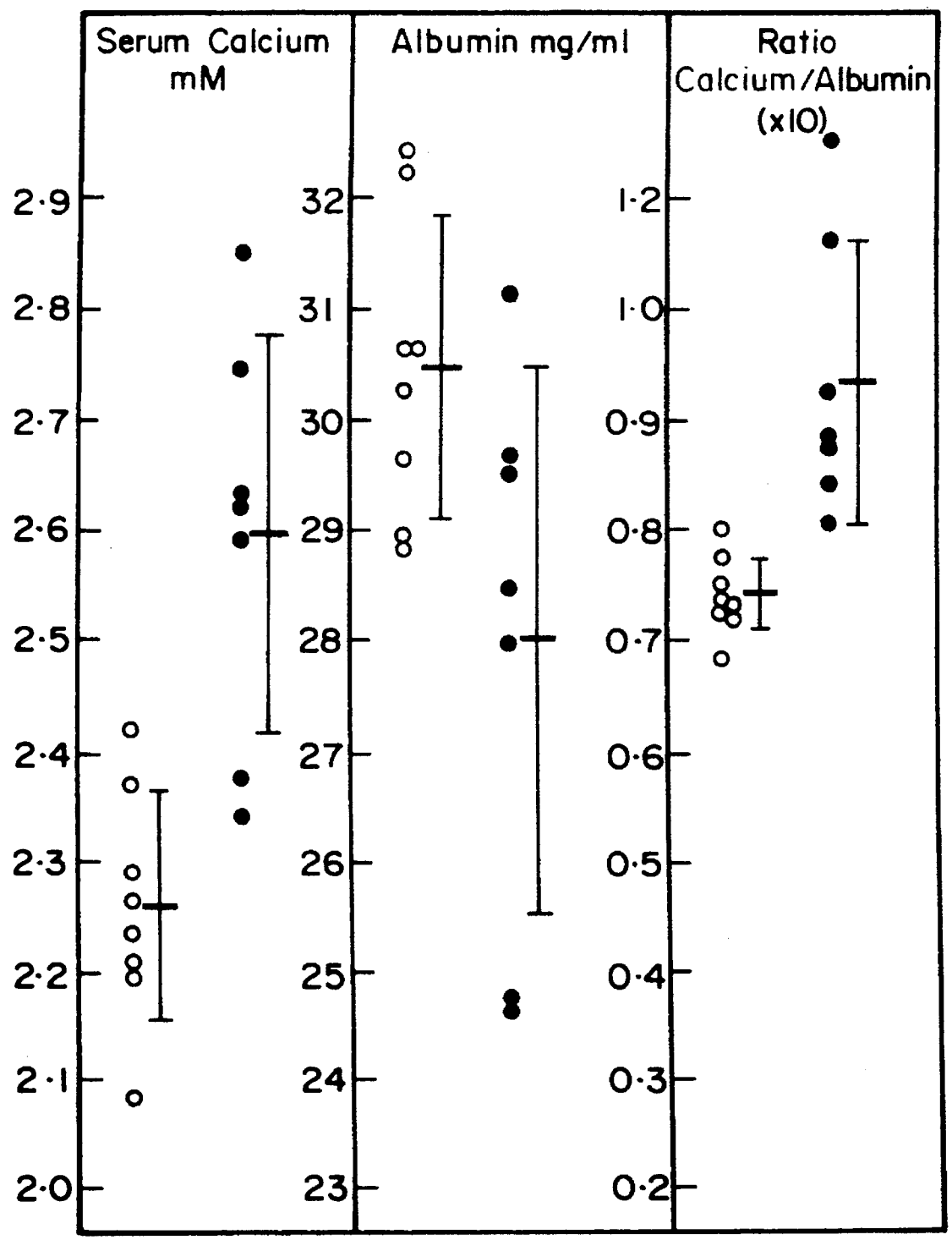
FIG. 3 is a graphical representation showing the elevation of serum calcium/albumin ratios in C3H/HeJ mice injected three times daily for 14 days with 2 µg LIF.

As shown in the typical example in FIG. 3, serum calcium levels were elevated in mice injected with 2 μg LIF for 14 days, the rises averaging 30% above values in control-injected mice. Elevated serum calcium levels were observed with as low a dose as 20 ng given once daily for 14 days (Table 2). In mice injected with 2 μg LIF three times daily elevated calcium levels were not present after 6 hours but were present after 3 days of injections.

Marrow, Spleen and Peritoneal Cell Changes

Table 3 summaries data from DBA/2 mice injected with 2 μg LIF three times daily for 14 days. For brevity, similar data from C3H/HeJ mice have not been detailed.

A uniform finding in mice of both strains was a fall of approximately 40% in total marrow cell numbers with a significant fall in the percentage of lymphoid cells and a small, but significant, rise in the percentage of mature granulocytes.

A minor weight increase was observed in the spleen of LIF-injected mice and, as shown in Table 3, in LIF-injected mice there was a significant fall in the percentage of lymphocytes and a significant rise in the percentage of nucleated erythroid cells and mature granulocytes.

Some variability was encountered between experiments in the total numbers of peritoneal cells in LIF-injected mice with no consistent trend being obvious. Injection of FCS/saline induced the appearance of significant numbers of eosinophils, presumably an immune response for the repeated injection of foreign protein and only becoming evident during the second week of injections. This eosinophil response was significantly lower or absent in LIF-injected mice. Conversely, LIF-injected mice exhibited a significant elevation in the percent of lymphocytes in peritoneal populations.

In all of the above parameters, the changes observed in LIF-injected C3H/HeJ mice were identical in direction and also statistically significant but usually were slightly smaller in magnitude.

In DBA/2 mice injected with 200 ng LIF, 1 to 3 times daily comparable but less marked changes in bone marrow cellularity were observed but interestingly spleen enlargement was more evident that with higher LIF doses (Table 2).

Megakaryocyte Changes

Figure 4A:
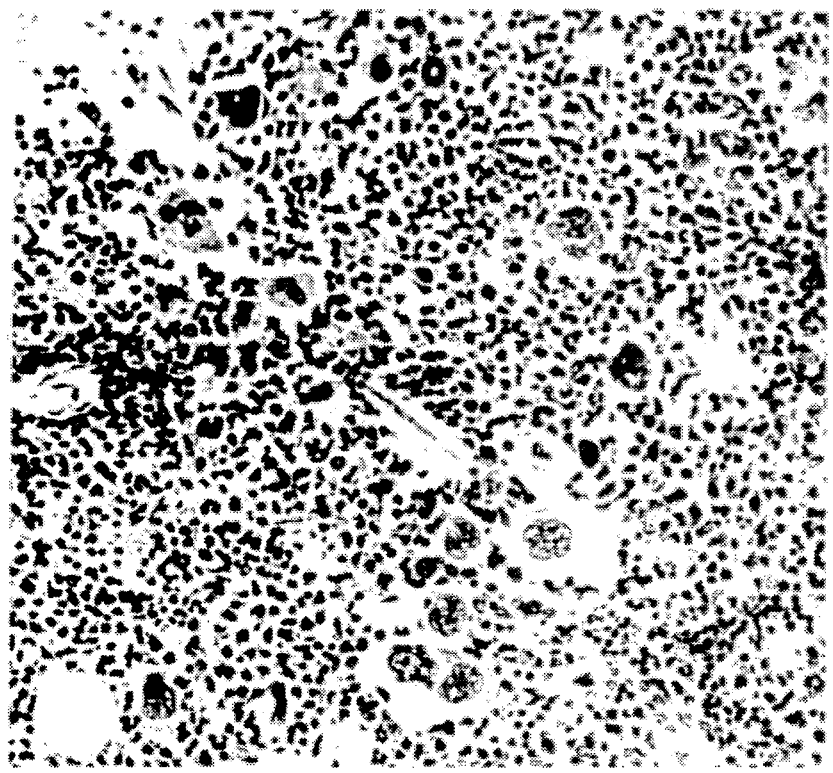
FIG. 4 is a pictorial representation showing the increase in megakaryocytes in the spleen of a DBA/2 mouse injected with 2 µg LIF 3 times daily for 14 days (A) versus spleen from a control mouse injected with FCS/saline (B). Haematoxylin and eosin (×250).
Figure 4B:
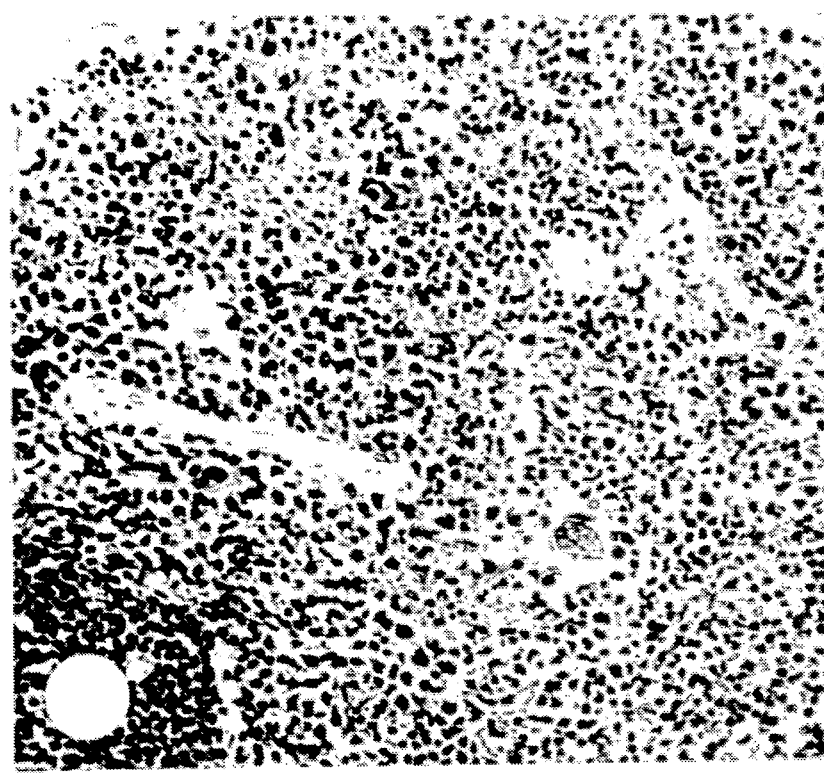

Because megakaryocytes were not adequately represented in cytocentrifuge preparations, counts of megakaryocyte numbers were made from sections of the spleen and sternal marrow segments. In both strains injected three times daily with 2 μg LIF for 14 days the frequency of megakaryocytes was significantly increased in the spleen (2–5-fold) (Table 4, FIG. 4) and significant elevation so lesser magnitude were observed in the sternal marrow.

Significant elevations of spleen megakaryocyte numbers were still detectable (3-fold) with as little as 20 ng LIF injected once daily for 14 days and megakaryocyte numbers were elevated in the spleen within 3 days of injecting 2 μg LIF three times daily (Table 2).

Progenitor Cell Changes in Marrow and Spleen

Figure 5:
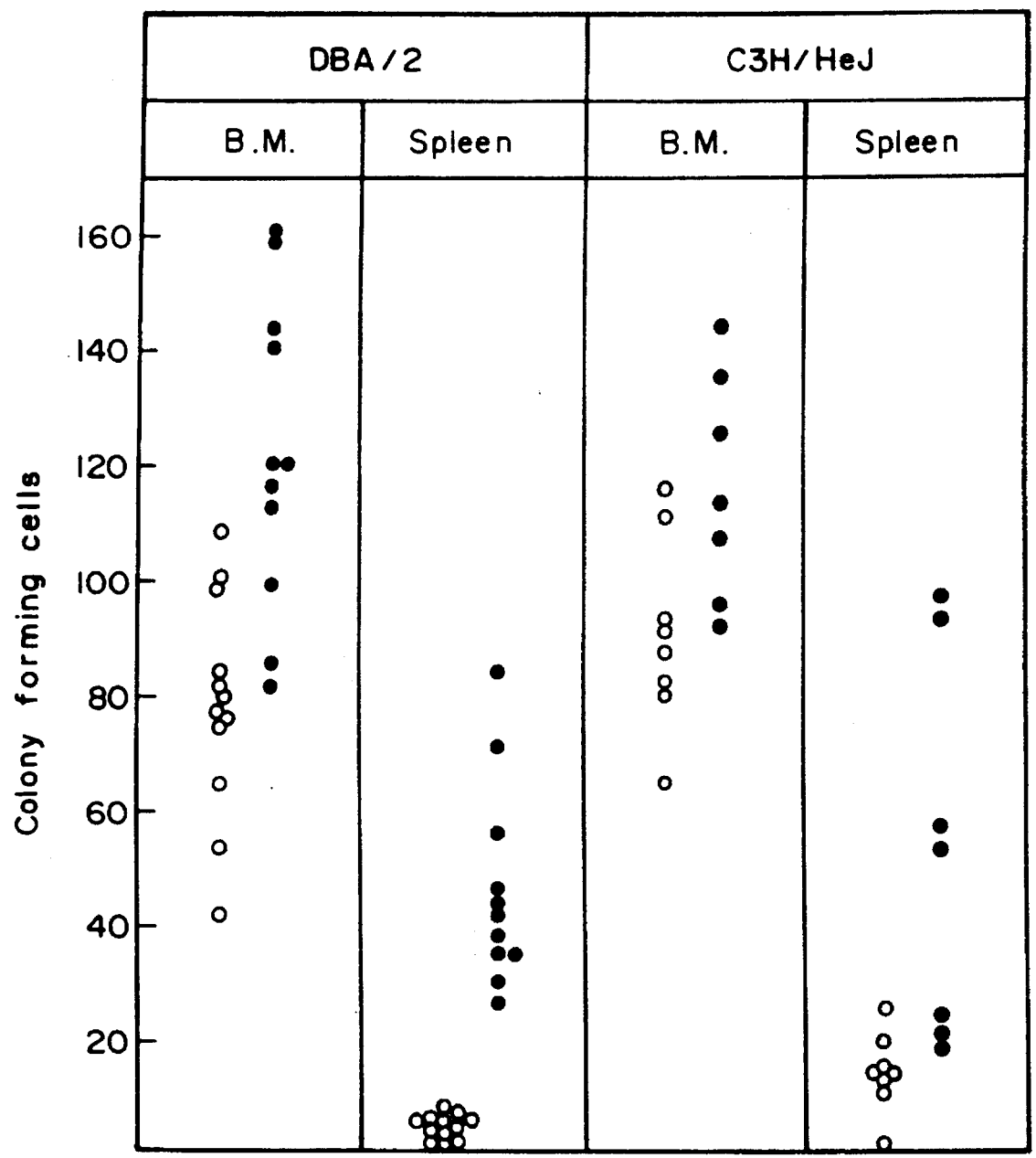
FIG. 5 is a graphical representation showing the increase in the frequency of progenitor cells in the marrow and spleen of mice injected with 2 µg LIF 3 times daily for 14 days (o) versus frequency in control mice injected with FCS/saline (o). Each point represents data from an individual animal.

The frequency of progenitor cells (exclusive of megakaryocyte progenitors) was significantly higher in the bone marrow of DBA/2 and C3H/HeJ mice injected with 2 μg LIF three times daily for 14 days than in the marrow of control-injected mice (FIG. 5). However, when these values were corrected for the fall in total marrow cellularity, total progenitor cell numbers were essentially unaltered by LIF injections.

In contrast, a marked rise in the frequency of progenitor cells was observed in the spleen of both strains injected with LIF. Since the overall size of the spleen was slightly increased, this indicates a rise in the absolute numbers of progenitor cells. Differential colony counts revealed no differences between LIF-injected and control mice in the relatively frequencies of the various subsets of progenitor cells: granulocytic, granulocyte-macrophage, macrophage, eosinophil, erythroid and mixed-erythroid progenitors.

The frequency of megakaryocyte colonies is not shown in the data in FIG. 5 and, to determine their frequency, counts were performed independently on acetylcholinesterase-stained cultures. The frequency of megakaryocyte progenitors was significantly higher in the marrow of LIF-injected mice than in control mice and 10-fold higher in the spleen of LIF-injected mice that in control mice (Table 4). When corrected for absolute cell numbers, there was little absolute rise in megakaryocyte progenitors in the marrow but in the spleen the rises were at least 10-fold.

Other Changes in LIF-Injected Mice

In mice injected with 2 μg LIF three times daily for 14 days, examination showed that the loss of body weight was ascribable to complete loss of subcutaneous and abdominal fat, a change that was also evident after only 3 days of injections. Liver and kidney weights were unaltered, indicating that the weight loss was not a true cachexia.

Mice receiving these doses of LIF exhibited pronounced thymus atrophy (Table 2) due to complete loss of cortical lymphocytes. No thymus weight loss was observed in mice injected with lower doses of LIF.

The liver showed no evidence of infiltration by haemopoietic cells, no increase in resident Kupffer cells, and no calcification. However, in mice receiving 2 μg LIF three times daily for 14 days there was a curious reduction in the number of parenchyma cell nuclei per unit area (eg in DBA/2 mice from 20±2 in control mice to 16±3 in LIF-injected mice, 0.01 (P<0.02)) with a corresponding increase in the area of nucleus-free cytoplasm. No pyknosis of liver cell nuclei was observed.

Small foci of calcium deposition was observed in the myocardium of 8 of 11 DBA/2 mice injected with 2 μg LIF versus 4 of 12 control mice, a slight but not significant difference.

No histological abnormalities were noted in the pancreas, ovaries, adrenal cortex or skeletal muscle comparable with those present in mice engrafted with LIF-producing cells.

In view of the marked excess new bone formation in mice engrafted with LIF-producing FDC-P1 cells (15,16), an analysis was made of the femur, tibia and sternum. No obvious new bone formation was observed in the femur or tibia as assessed by unusual trabeculae formation. However, analysis of sternal segments indicated a significant thickening of the bone cortex in LIF-injected DBA/2 mice. In mice injected with 2 μg LIF 3 times daily for 14 days the area occupied by bone cortex was 30.4±4.2% of the total area of sternal segments versus 23.1±5.6% in control mice (P<0.01). However, in C3H/HeJ mice given the same LIF dosage the figures were 23.1±5.3% versus 21.4±4.4, a not significant differences.

EXAMPLE 3

Effect of LIF and II-3

Seven-day cultures of marrow cells containing 100 Units/ml of LIF showed no megakaryocyte or other colony formation and no surviving single megakaryocytes. In cultures containing combinations of LIF (1000 Units/ml) with 1000 Units/ml of GM-CSF, G-CSF or M-CSF, again no colonies containing megakaryocytes were observed nor were there single surviving megakaryocytes.

Figure 6:
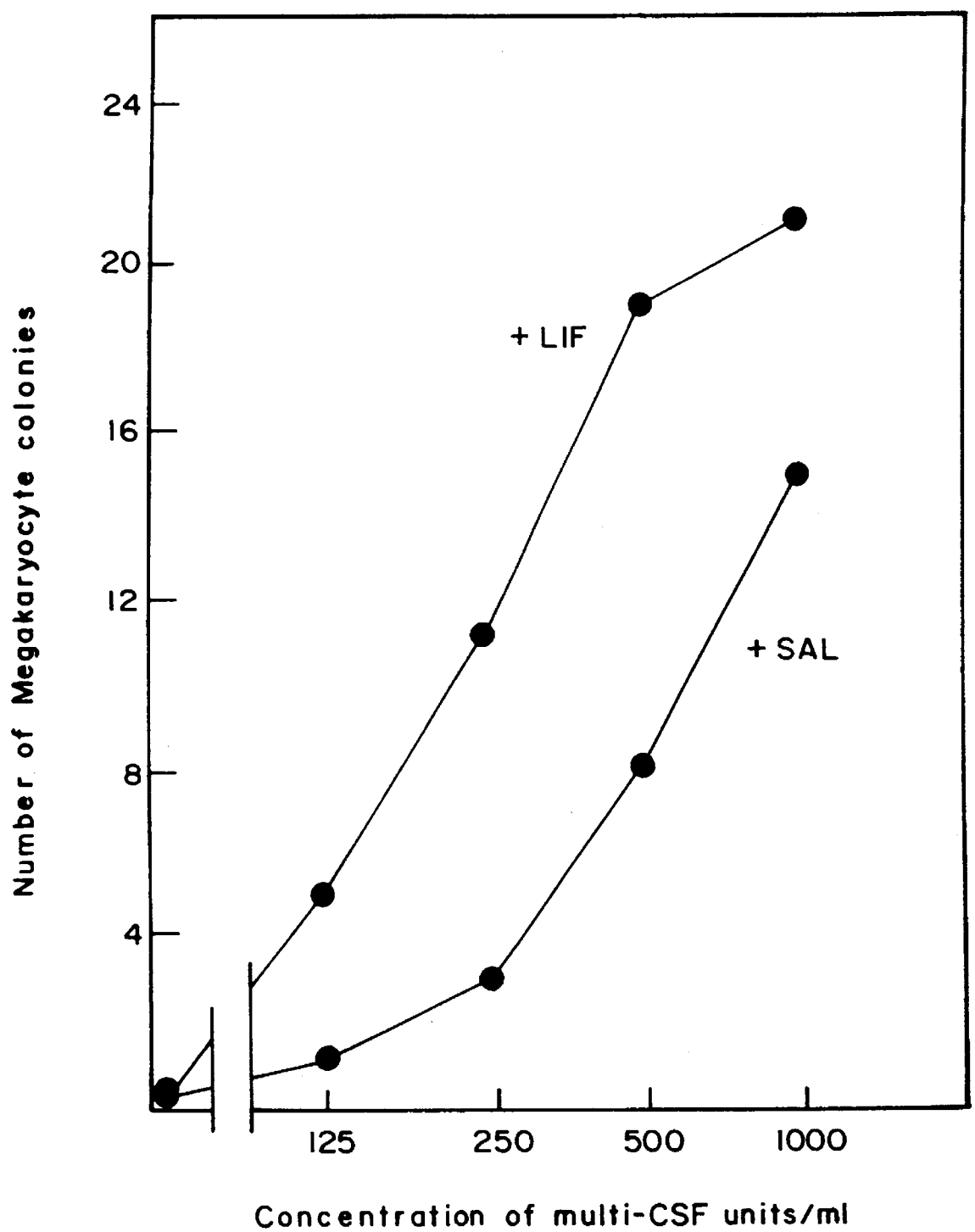
FIG. 6 is a graphical representation showing enhancement of megakaryocyte colony formation in IL-3 stimulated cultures of 50,000 of C3H/HeJ marrow cells by inclusion of 1000 units per ml of LIF. Each point represents mean values from duplicate cultures.
Figure 7:
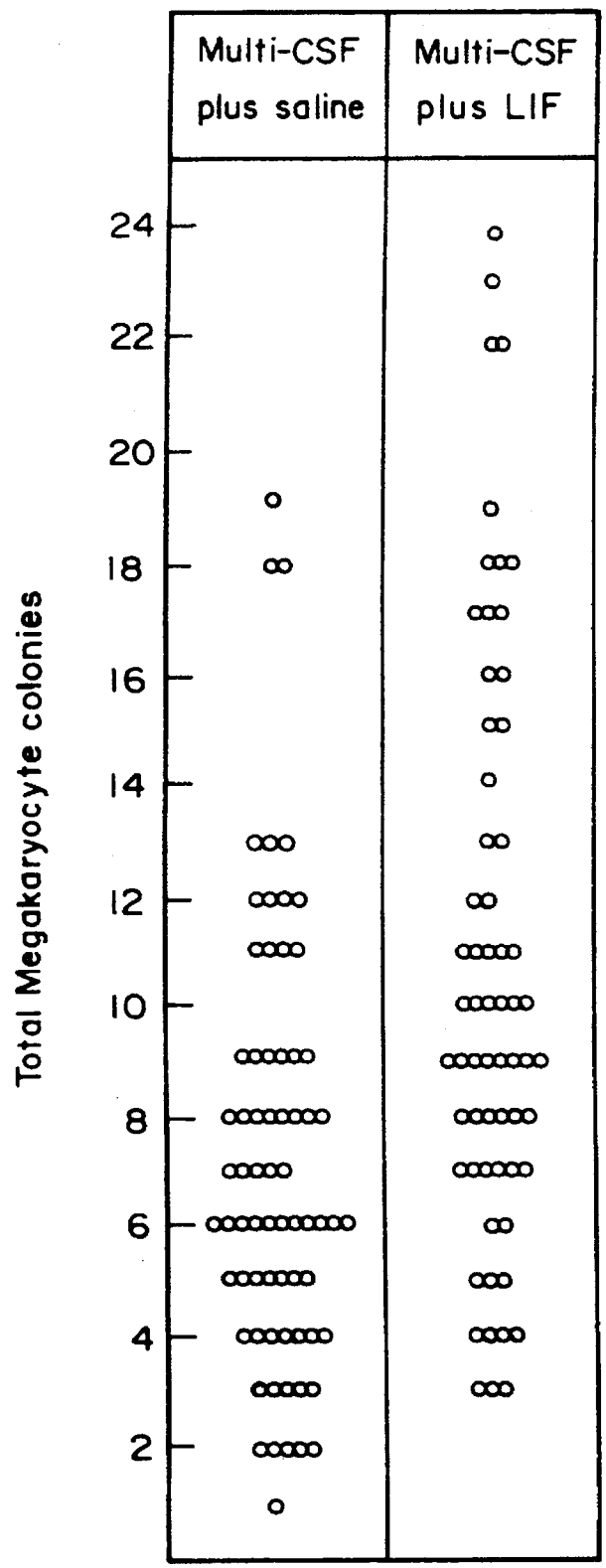
FIG. 7 is a graphical representation showing pooled data from 18 separate experiments on megakaryocyte colony formation in cultures of 50,000 C3H/HeJ marrow cells stimulated either by 500 units per ml IL-3 plus 0.1 ml saline or 500 units per ml IL-3 plus 1000 units per ml LIF. Each point represents the number of colonies in a single culture dish.

In marrow cultures containing from 125 to 1000 Units/ml of IL-3, megakaryocyte colony formation was observed. These colonies usually were of two types—those containing small numbers of large dispersed megakaryocytes or large colonies containing acetylcholine-positive cells of various sizes. Less frequently, mixed colonies were observed containing megakaryocytes together with cells of other lineages and typically in these colonies the number of acetylcholinesterase-positive cells was relatively small. Inclusion of 1000 Units of LIF in such cultures increased the number of megakaryocyte colonies developing with all concentrations of IL-3 (FIG. 6). Data on megakaryocyte colony numbers from 18 separate experiments using 500 Units of IL-3 indicated that in individual cultures, the number of megakaryocyte colonies varied widely. In the same 18 experiments, in cultures containing 500 Units of IL-3 plus 1000 Units/ml of LIF, a significant overall increase in megakaryocyte colony numbers was observed (FIG. 7) (t-4.43, P<0.01) despite the variation between individual cultures.

Combination of LIF with IL-3 had no influence on the number or size of granulocyte-macrophage colonies developing in these cultures compared with cultures containing IL-3 alone. To document that this enhanced colony formation actually resulted in the production of more megakaryocytes, total megakaryocyte numbers were determined by counting colony megakaryocytes in the entire culture dish in fourteen experiments using 500 Units IL-3 alone or in combination with 1000 Units of LIF. In counts on 50 unselected cultures of each type, the addition of LIF significantly increased the total number of megakaryocytes developing per culture from 183±122 to 300±185 (±SD) (t=3.79, p<0.01).

Figure 8:
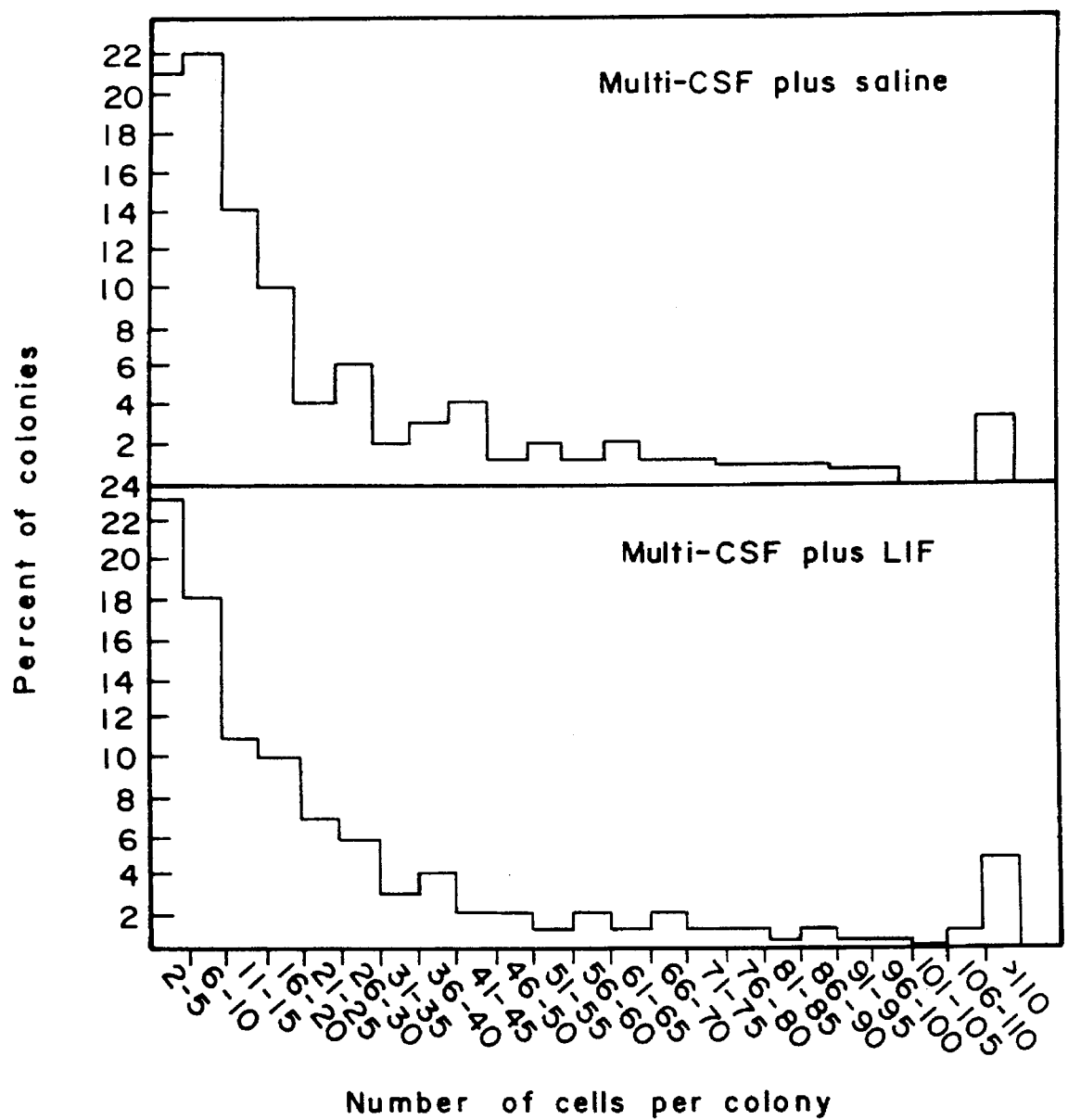
FIG. 8 is a graphical representation showing the distribution analysis of the absolute number of megakaryocytes in colonies wholly or partly composed of megakaryocytes, sequential analysis of 444 colonies stimulated by 500 units per ml IL-3 plus 0.1 ml saline and 565 colonies stimulated by 500 units per ml IL-3 plus 1000 units per ml LIF.

The frequency distribution of megakaryocyte numbers in individual colonies was analysed to determine whether LIF might exert a selective effect on the size of small colonies of mature cells or on the larger colonies containing megakaryocytes at varying stages of maturation. The histogram in FIG. 8 shows the frequency distribution of colonies containing small or large numbers of megakaryocytes. The addition of LIF did not appear to result in an exclusive increase in frequency of any particular subset of megakaryocytecontaining colonies.

EXAMPLE 4

Receptors for LIF on Megakaryocytes

Figure 9:
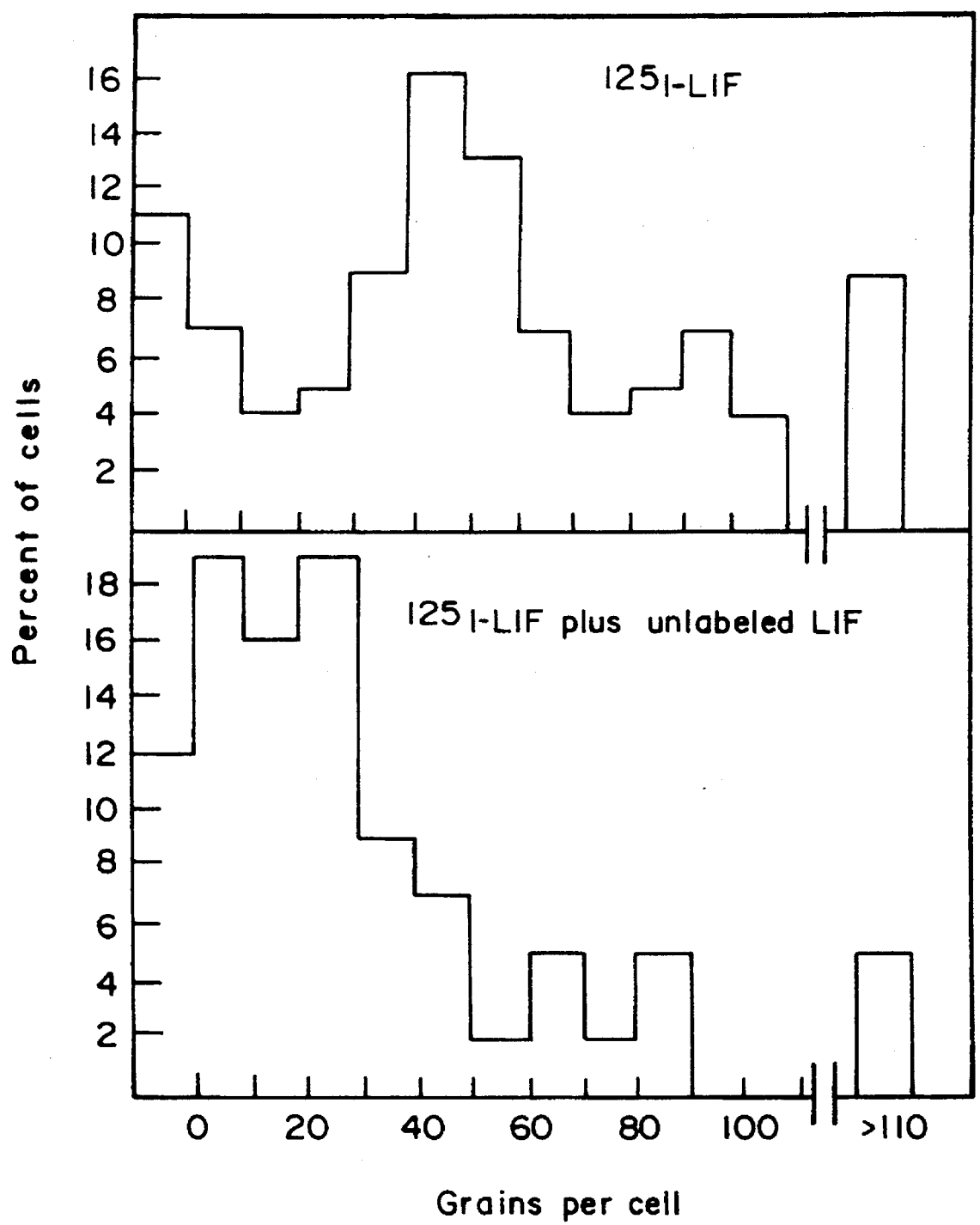
FIG. 9 is a graphical representation showing the frequency distribution of grain counts in autoradiographs of marrow megakaryocytes binding $^{125}$I-LIF with or without an excess of unlabelled LIF.

Marrow suspensions enriched for megakaryocytes were incubated in vitro with $^{125}$I-labelled LIF with or without a 20-fold excess of unlabelled LIF. As shown in FIG. 9, labelling was exhibited by approximately 85% of megakaryocytes. In the presence of an excess of unlabelled LIF, labelling was significantly reduced by not eliminated. This suggests that part of the observed labelling may have been non-specific and in this context it was evident that damaged megakaryocytes exhibited prominent labelling that was not blocked by unlabelled LIF. It was also evident that mature megakaryocytes exhibited higher grain counts than less mature cells with basophilic cytoplasm (mean grain count for mature cell=80±50 versus immature cells 11±14 grains per cell).

EXAMPLE 5

Effect of LIF on Blood Platelet Number in Monkeys

Materials and Methods

Animals

Eight adult Rhesus monkeys, Macaca mulatta of both sexes, approximately 6 to 10 years old, weighing 6 to 11 kg, were individually housed. Monkeys were provided with 10 changes per hour of fresh air conditioned to 23° C.±2° C. with a relative humidity of 60% ±10. They were maintained in a 12 hour light/dark cycle and were provided with tap water ad libitum and commercial primate chow and fruits.

| LIF dosages and treatment schedule | | |
|---|---|---|
| Monkey No. | Sex | Dose of rhLIF (µg/kg/day 0–13) |
| B62 | male | 50 |
| B10 | female | 50 |
| D13 | male | 10 |
| 645 | female | 10 |
| C78 | male | 2 |
| V143 | female | 2 |
| C48 | male | — |
| D41 | female | — |
| C87 | male | — |

Administration of rhLIF

Frozen stock solutions of rhLIF provided by Dr. Nicos Nicola, (The Walter and Eliza Hall Institute of Medical Research, Melbourne, Australia), were divided into the daily amounts and stored at −70° C., again. The daily amounts were thawed and diluted with 4 ml saline supplemented with 0.5% monkey serum. Daily doses of the cytokine were divided into two administrations and injected subcutaneously (s.c.) between 8 and 9 am and 4 and 5 pm. Samples for determining biological activity were retained at the beginning and at the end of the treatment period. Control monkeys received s.c. injections of non-pyrogenic saline supplemented with 0.5% monkey serum.

Hematologic Examinations

Peripheral blood was collected for hematologic examinations in EDTA-coated tubes before treatment began, either daily or at two day intervals during the treatment period, and three times a week during the post-treatment period.

Parameters measured included the total count of red blood cells (RBC), white blood cells (WBC), platelets, and determination of hemoglobin and hematocrit (Sysmex 2000, TOA: Tokyo, Japan). Differential blood cell counts were established as normal for Rhesus monkeys (23) on the examination of 200 cells of Giemsa-stained blood smears by two independent observers.

Results

Elevation of Blood Platelet Counts

Figure 10:
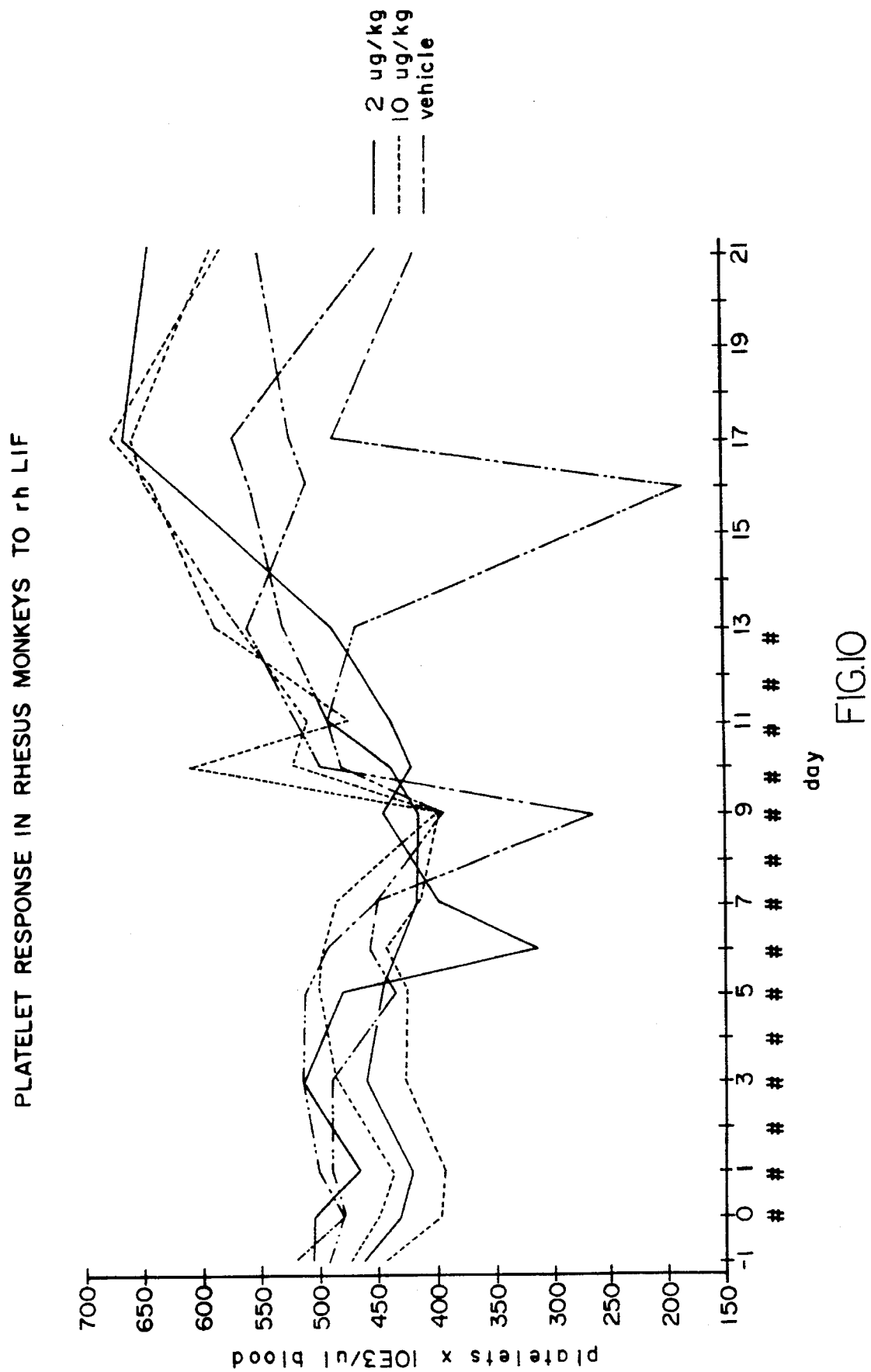
FIG. 10 is a graphical representation showing the the platelet response to rhLIF in Rhesus monkeys.

As shown in FIG. 10, one of the animals receiving a daily dose of 2 µg LIF/kg showed a rise in blood platelet counts at the end of the two week treatment period. Maximum platelet counts 1.4 fold elevated above normal levels were determined around day 5 after termination of the LIF administration. The other animal in the 2 µg dose group showed a minor rise in platelet counts. The two monkeys receiving a daily dose of 10 µg LIF/kg for two weeks responded with a maxiumum rise in platelet counts of approximately 1.5 fold above basal levels. As shown in FIG. 11, animals treated with a daily dose of 50 µg LIF/kg responded with an earlier rise in platelet counts beginning on day 2–3 after the initiation of treatment, with maxiumum levels in the range of 2–3 fold above normal levels at the end of the administration period.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

TABLE 1

Changes in the Peripheral Blood After the Injection of LIF

| Parameter | DBA/2 | | | C3H/HeJ | | |
|---|---|---|---|---|---|---|
| | Normal (n = 4) | FCS/Sal (n = 12) | LIF (n = 11) | Normal (n = 4) | FCS/Sal (n = 8) | LIF (n = 7) |
| WBCs/μL | 5,760 ± 1,810 | 5,890 ± 230 | 5,040 ± 1,260 | 3,950 ± 1,300 | 3,010 ± 1,140 | 3,410 ± 960 |
| Neutrophils/μL | 840 ± 230 | 780 ± 410 | 1,120 ± 430 | 1,070 ± 710 | 700 ± 320 | 980 ± 380 |
| Hematocrit % | 46 ± 1 | 46 ± 2 | 42 ± 3 | 45 ± 1 | 43 ± 1 | 41 ± 3 |
| Platelets/μL × $10^6$ | 1.01 ± 0.08 | 1.09 ± 0.10 | 1.82 ± 0.13 | 0.80 ± 0.10 | 0.92 ± 0.15 | 1.78 ± 0.19 |
| ESR | 1.4 ± 0.3 | — | — | 1.0 ± 0.7 | 1.2 ± 0.7 | 4.1 ± 1.0 |

Mice were examined on day 15 after the injection of 2 μg LIF three times daily for 14 days. Mean values ± SDs.
Abbreviation: ESR, erythrocyte sedimentation rate.

TABLE 2

Effects of Dose and Duration of LIF Injections on Responses Observed

| Mouse Strain | Dose Schedule of LIF or FCS/Sal | Body Weight (g) | Thymus Weight (mg) | Spleen Weight (mg) | Spleen Mega-karyocytes | Platelets (×$10^6$/μL) | ESR | Ratio Calcium/ Albumin (mmol/L/ mgmL$^{-1}$ × 10) |
|---|---|---|---|---|---|---|---|---|
| DBA/2 | 2 μg × 3 14 d | 20.6 ± 0.8 | 10 ± 5* | 107 ± 14 | 442 ± 134* | 1.82 ± 0.13* | — | 0.95 ± 0.04* |
| | FCS/Sal × 3 14 d | 20.5 ± 1.2 | 35 ± 2 | 92 ± 14 | 93 ± 42 | 1.09 ± 0.10 | — | 0.82 ± 0.09 |
| | 200 ng × 3 14 d | 21.5 ± 1.1 | 36 ± 6 | 149 ± 5* | 286 ± 30* | 1.39 ± 0.17* | 4.2 ± 1.3 | 0.85 ± 0.05 |
| | FCS/Sal × 3 14 d | 20.6 ± 0.7 | 34 ± 2 | 92 ± 20 | 61 ± 15 | 0.96 ± 0.08 | 2.7 ± 1.4 | 0.77 ± 0.05 |
| | 200 ng × 2 14 d | 21.5 ± 0.8 | 37 ± 5 | 146 ± 10* | 226 ± 89* | 1.20 ± 0.08* | 4.0 ± 1.1* | 0.85 ± 0.03 |
| | FCS/Sal × 2 14 d | 20.7 ± 0.9 | 40 ± 4 | 99 ± 9 | 83 ± 23 | 0.88 ± 0.09 | 1.2 ± 0.3 | 0.79 ± 0.05 |
| | 200 ng × 1 14 d | 19.3 ± 1.3 | 51 ± 10 | 130 ± 24 | 82 ± 39 | 1.15 ± 0.17* | 4.5 ± 1.7 | 1.05 ± 0.08 |
| | 20 ng × 1 14 d | 19.0 ± 1.0 | 47 ± 3 | 123 ± 24 | 108 ± 38* | 0.93 ± 0.07 | 2.0 ± 1.6 | 1.02 ± 0.06 |
| | FCS/Sal × 1 14 d | 19.3 ± 0.7 | 50 ± 6 | 100 ± 26 | 31 ± 11 | 0.79 ± 0.09 | 2.8 ± 1.2 | 0.91 ± 0.02 |
| | 10 ng × 1 14 d | 21.3 ± 0.4 | 33 ± 1 | 101 ± 12 | 123 ± 40 | 0.91 ± 0.11 | 1.6 ± 0.9 | 0.82 ± 0.07 |
| | 2 ng × 1 14 d | 21.6 ± 1.1 | 43 ± 11 | 97 ± 17 | 111 ± 44 | 0.98 ± 0.14 | 1.0 ± 0.4 | 0.71 ± 0.06 |
| | FCS/Sal × 1 14 d | 21.8 ± 1.5 | 40 ± 8 | 103 ± 7 | 93 ± 14 | 0.87 ± 0.17 | 1.2 ± 0.3 | 0.78 ± 0.03 |
| C3H/HeJ | 2 μg × 3 14 d | 16.2 ± 1.9* | 9 ± 2* | 93 ± 31 | 148 ± 107* | 1.78 ± 0.19* | 4.1 ± 1.0* | 0.93 ± 0.13* |
| | FCS/Sal × 3 14 d | 19.7 ± 1.4 | 30 ± 4 | 101 ± 20 | 76 ± 48 | 0.92 ± 0.15 | 1.2 ± 0.7 | 0.74 ± 0.03 |
| | 2 μg × 3 3 d | 16.8 ± 1.6 | 14 ± 5* | 94 ± 31 | 131 ± 72 | 0.82 ± 0.05 | 5.7 ± 2.4* | 0.98 ± 0.09 |
| | FCS/Sal × 3 3 d | 18.4 ± 0.3 | 30 ± 6 | 94 ± 18 | 49 ± 22 | 0.87 ± 0.11 | 1.9 ± 0.9 | 0.84 ± 0.02 |
| | 2 μg × 1 6 h | — | — | — | — | 0.95 ± 0.07 | 1.8 ± 0.6 | 0.94 ± 0.02 |
| | FCS/Sal × 1 6 h | — | — | — | — | 0.90 ± 0.07 | 0.9 ± 1.2 | 0.84 ± 0.05 |

Four to eight mice were used per group. Data from individual experiments with LIF-injected mice are listed in groups with their corresponding control mice injected with FCS/saline listed on the following line. The frequency of injections per day is indicated: eg, × 3. Values recorded are mean values ± SDs. The methods for deriving estimates of spleen megakaryocytes, erythrocyte sedimentation rates (ESR), and serum calcium/albumin ratios are detailed in Materials and Methods.
*Values differing significantly from control values (P < .01).

TABLE 3

LIF-Induced Changes in Marrow Spleen and Peritoneal Cell Populations of DBA/2 Mice

| Organ | Injected With | Total Cells (×10$^6$) or Spleen Weight (mg) | Mean Percent | | | | | | |
|---|---|---|---|---|---|---|---|---|---|
| | | | Blasts | Promyelo-cytes Myelocytes | Meta-myelocytes Polymorphs | Lymphocytes | Monocytes | Eosinophils | Nucleated Erythroid Cells |
| Bone Marrow | LIF | 11.0 ± 1.8* | 4.9 ± 3.2 | 7.8 ± 2.6 | 36.3 ± 5.6* | 14.0 ± 3.1* | 6.8 ± 2.4 | 4.8 ± 2.9 | 25.4 ± 4.6 |
| | FCS/Sal | 18.5 ± 3.5* | 2.8 ± 1.5 | 7.8 ± 2.7 | 28.5 ± 4.3* | 23.8 ± 3.4* | 5.6 ± 2.6 | 5.8 ± 2.3 | 25.7 ± 5.7 |
| Spleen | LIF | 107 ± 14 | 3.7 ± 1.4 | 1.9 ± 2.1 | 3.9 ± 2.8* | 54.1 ± 11.5* | 1.6 ± 1.2 | 0.9 ± 1.8 | 33.9 ± 11.2* |
| | FCS/Sal | 92 ± 14 | 2.7 ± 1.2 | 0.4 ± 0.7 | 1.3 ± 1.1* | 77.6 ± 6.7* | 1.1 ± 1.0 | 0.9 ± 1.0 | 16.0 ± 5.4* |
| Peritoneal Cells | LIF | 23.3 ± 15.7 | | | 3.5 ± 9.2 | 48.0 ± 9.5* | 45.8 ± 9.9* | 2.6 ± 1.5* | |
| | FCS/Sal | 13.2 ± 6.9 | | | 1.3 ± 2.2 | 14.4 ± 6.4* | 65.7 ± 9.3* | 18.3 ± 12.0* | |

Data from 12 mice of each type examined after 14 days of injections of 2 μg LIF three times daily. Mean values ± SDs.
*Data differing significantly (P < .01).

TABLE 4

Effect of LIF on Megakaryocyte Progenitors and Megakaryocytes

| Parameter | DBA/2 | | C3H/HeJ | |
|---|---|---|---|---|
| | LIF | FCS/Sal | LIF | FCS/Sal |
| Megakaryocyte Progenitors | | | | |
| Bone marrow | 8.4 ± 3.7* | 5.1 ± 2.1* | 6.6 ± 2.1* | 3.4 ± 2.0* |
| Spleen | 3.9 ± 3.7* | 0.4 ± 0.5* | 5.9 ± 5.1* | 0.6 ± 0.5* |
| Megakaryocytes | | | | |
| Bone marrow | 9.6 ± 1.3* | 5.0 ± 1.1* | 4.4 ± 1.0* | 3.0 ± 0.7* |
| Spleen | 442 ± 134* | 93 ± 42* | 148 ± 107 | 76 ± 48 |

Mice were injected three times daily with 2 μg LIF for 14 days. Progenitor cells were estimated from cultures of 2.5 × 10$^4$ cells. Megakaryocytic numbers are number per sternal marrow segment or spleen section corrected for area. Mean values ± SDs from eight mice of each type.
*Indicate significantly different values (P < .01).

REFERENCES

1. Tomida M, Yamamoto-Yamiguchi Y, Hozumi M, *J Biol Chem* 259: 10978, 1984.
2. Hilton DJ, Nicola NA, Gough NM, Metcalf D, *J Biol Chem* 263: 9238, 1988.
3. Gearing DP, Gough NM, King JA, Hilton DJ, Nicola NA, Simpson RJ, Nice EC, Kelso A, Metcalf D, *EMBO J* 6: 3995, 1987.
4. Maekawa T, Metcalf D, *Leukemia* 3: 270, 1989.
5. Metcalf D, Hilton DJ, Nicola NA, *Leukemia* 2: 216, 1988.
6. Moreau J-F, Donaldson DD, Bennett F, Witek-Gianotti JA, Clark SC, Wong GG, *Nature* 336: 690, 1988.
7. Hilton DJ, Nicola NA, Metcalf D, *Proc Natl Acad Sci USA* 85: 5971, 1988.
8. Hilton DJ, Nicola NA, Metcalf D, *J Cell Physiol* (in press).
9. Abe E, Tanaka H, Ishimi Y, Miyaura C, Hayashi T, Nagasawa H, Tomida M, Yamaguchi Y, Hozumi M, Suda T, *Proc Natl Acad Sci USA* 83: 5958, 1986.
10. Williams RL, Hilton DJ, Pease S, Willson TA, Stewart CL, Gearing DP, Wagner EP, Metcalf D, Nicola NA, Gough NM, *Nature* 336: 684, 1988.
11. Smith Ag, Heath JK, Donaldson DD, Wong GG, Moreau J, Stahl M, Rogers D, *Nature* 336: 688, 1988.
12. Baumann H, Won K-A, Jahreis GP, *J Biol Chem* 264:8046, 1989.
13. Baumann H, Wong GG, *J Immunol* 143:1163, 1989.
14. Mori M, Yamaguchi K, Abe K, *Biochem Biophys Res Commun* 160:1085, 1989.
15. Metcalf D, Gearing DP, *Proc Natl Acad Sci USA* 86:5948, 1989.
16. Metcalf D, *Leukemia* (in press).
17. Metcalf D, Elsevier Amsterdam, 1984.
18. Metclaf D, Begley CG, Johnson GR, Nicola NA, Lopez AF, Williamson DJ, *Blood* 68:46, 1986.
19. McDonald TP, *Exp Hematol* 16:210, 1988.
20. Lotem J, Shabo Y, Sachs L, *Blood* 74:1545, 1989.
21. Ishibashi T, Kimura H, Shikama Y, Uchida T, Kariyone S, Hirano T, Kishimoto T, Takatsuki F, Akiyama Y, *Blood* 74:1241, 1989.
22. Yamamuri T et al., *Science* 246:1412, 1989.
23. Huser HD (ed), Atlas of comparative primate hematology. Part I: Normal Hematology. New York, Academic Press, p. 85, 1970.

I claim:

1. A method for treating thrombocytopenia in a mammal which method comprises administering to said mammal an effective amount of Leukaemia Inhibitory Factor (LIF) for a time and under conditions sufficient to increase the level of formation of megakaryocytes or their progenitors or increase the level of platelets.

2. The method according to claim 1 which further comprises administering LIF in simultaneous or sequential combination with one or more other cytokines having megakaryocytopoietic or thrombocytopoietic activity.

3. The method according to claim 2 wherein the other cytokine comprises at least one of interleukin-3 (IL-3), thrombopoietin and interleukin-6 (IL-6).

4. The method according to claim 3 wherein the other cytokine is IL-3.

5. The method according to any one of claims 1–4 wherein the LIF and other cytokine is of human, murine or livestock origin.

6. The method according to claim 5 wherein the LIF and other cytokine are prepared by recombinant or synthetic means.

7. The method according to claim 1 wherein the mammal is human or a livestock animal.

8. The method according to claim 1 wherein the route of administration is by the intravenous, interperitoneal, intramuscular or subcutaneous route.

9. A pharmaceutical composition for treating thrombocytopenia, comprising an effective amount of LIF in combination with at least one of IL-3, thrombopoietin and IL-6, admixed with a pharmaceutically acceptable carrier.

10. The composition according to claim 9 comprising LIF in combination with IL-3, admixed with a pharmaceutically acceptable carrier.

* * * * *